US006737421B1

(12) United States Patent
Lubish et al.

(10) Patent No.: US 6,737,421 B1
(45) Date of Patent: May 18, 2004

(54) CYCLO-ALKYL SUBSTITUTED BENZIMIDAZOLES AND THEIR USE AS PARP INHIBITORS

(75) Inventors: Wilfried Lubish, Heidelberg (DE); Michael Kock, Schifferstadt (DE); Thomas Hoeger, Edingen-Neckarhausen (DE); Roland Grandel, Dossenheim (DE); Sabine Schult, Speyer (DE); Reinhold Mueller, Schifferstadt (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/959,161

(22) PCT Filed: Apr. 11, 2000

(86) PCT No.: PCT/EP00/03231

§ 371 (c)(1),
(2), (4) Date: Apr. 4, 2002

(87) PCT Pub. No.: WO00/64878

PCT Pub. Date: Nov. 2, 2000

(30) Foreign Application Priority Data

Apr. 22, 1999 (DE) ........................................ 199 182 116

(51) Int. Cl.$^7$ .................... C07D 235/06; C07D 403/08; C07D 401/08; A61K 31/4184
(52) U.S. Cl. .................. 514/218; 514/254.06; 514/322; 514/338; 514/394; 540/553; 540/574; 544/370; 546/199; 546/273.4; 548/306.1; 548/309.7
(58) Field of Search .......................... 548/306.1, 309.7; 546/199, 273.4; 544/370; 540/553, 574; 514/218, 254.06, 322, 338, 394

(56) References Cited

U.S. PATENT DOCUMENTS

| 4,176,184 A | 11/1979 | Aistel et al. ................. 424/248 |
| 4,763,262 A | 8/1988 | Leiber ........................ 364/426 |

FOREIGN PATENT DOCUMENTS

| DE | 26 49 125 | 1/1978 |
| DE | 27 32 951 | 2/1979 |
| DE | 35 22 230 | 1/1987 |
| DE | 38 30 060 | 3/1990 |
| JP | 5-222000 | * 8/1993 |
| WO | 35 46 575 | 10/1987 |
| WO | WO 94/12461 | 6/1994 |
| WO | WO 97/04771 | 2/1997 |
| WO | WO 97/48697 | 12/1997 |
| WO | WO 98/06703 | 2/1998 |
| WO | WO 98/33802 | 8/1998 |

OTHER PUBLICATIONS

Cuzzocrea et al. "Beneficial effects of 3-aminobenzamide, an inhibitor of poly (ADP-ribose) synthetase in a rat model of splanchnic artery occlusion and reperfusion" British J. Pharmacology vol. 121, (1997) pp. 1065–1074.

Cuzzocrea et al. "Protective effects of 3-aminobenzamide, an inhibitor of poly (ADP-ribose) synthase in a carrageenan-induced model of local inflammation" European J. Pharmacology vol. 342, (1998) pp. 67–76.

Szabo et al. "Protection agains peroxynitrite-induced fibroblast injury and arthritis development by inhibition of poly-(ADP-ribose) synthase" Proc. Natl. Acad. Sci. USA vol. 95 (1998) pp. 3867–3872.

Ehrlich et al. "Inhibition of the induction of collagenase by interleukin-1β in cultured rabbi synovial fibroblasts after treatment with the poly(ADP-ribose)-polymerase inhibitor 3-aminobenzaimde" Rhumatol Int. vol. 15 (1995) pp. 171–172.

Kröger et al. "Synergistic effects of Thalidomide and Poly-(ADP-Ribose) Polymerase Inhibition on Type II Collagen-Induced Arthritis in Mice" Inflammation vol. 20 No. 2 (1996) pp. 203–215.

Weltin et al. "Immunosuppressive Activities of 6(5H)-Phenanthridinone A New Poly(ADP-Ribose) Polymerase Inhibitor" Int. J. Immunopharmac vol. 17 No. 4, (1995) pp. 265–271.

Chen et al. "Potentation of the antitumor activity of cisplatin in mice by 3-aminobenzamide and nicotinamide" Chander Chemother Pharmacol vol. 22, (1988) pp. 303–307.

(List continued on next page.)

Primary Examiner—Deepak Rao
(74) Attorney, Agent, or Firm—Wood, Phillips, Katz, Clark & Mortimer

(57) ABSTRACT

Compounds of the formula I or II

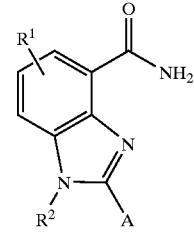

I

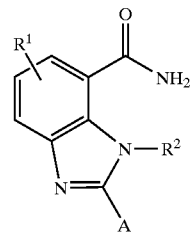

II and their tautomeric forms, possible enantiomeric and diastereomeric forms, possible cistrans isomers on the rings in A and prodrugs thereof, pharmaceutical compositions containing these compounds and methods of treating neurodegenerative diseases or neuronal damage with these compounds.

23 Claims, No Drawings

OTHER PUBLICATIONS

Burkhart et al. "Mice lacking the poly(ADP–ribose) polymerase gene are resistant to pancreactic beta–cell destruction and diabetes development induced by streptozocin" Nature Medicine vol. 5, (1999) pp. 314–319.

Jerchl et al. "Zur Darstellung der Benzimidazole" Annalen Der Chemie Band 573, (1951) pp. 162–173.

Denny et al. "Potential Antitumor Agents. 59. Structure–activity relationships for 2–phenylbenzimidazole–4–carboxamides, a New Class of "Minimal" DNA–Intercalcating Agents Which May Not Act Via Topoisomerase II" J. Med. Chem. vol. 33 (1990) pp. 814–819.

Gilchrist et al. "Cyclisation of ortho–Substituted N–Arylbenzamidoyl Nitrenes. Part 2. Preferential Cyclisations at and *ortho*–Position Bearing a Methoxycarbonyl Group" J. Chem. Soc. Perkin Trans. (1979) pp. 2303–2307.

Senner et al. "Synthesis and Structure–Activity Relationships of Some 2,5–Disubstituted Benzoxazoles and Benzimidazoles as Antimicrobial Agents" II Farmco vol. 52 (1997) pp. 99–103.

Hein et al. "The use of Polyphosphoric Acid in the Synthesis of 2–Aryl– and 2–Alkyl–substituted Benzimidazoles, Benzoxazoles and Benzothiazoles" J. Amer. Chem. Soc. (1957) pp. 427–429.

Benchidmi et al. "Nitration de Benzimidazoles Substitues" Bull. Soc. Chim. Bieg. vol. 104 (1995) pp. 605–611.

Bamberger "Studienüber Imidazole" Annalen der Chemie Band 273 (1893) p. 320.

Thiermann et al. "Inhibitors of PARS Activity Reduce Infarct Sin in a Rabbit Model of Regional Myocardial Ischemia and Reperfusion" Proc. Natl. Acad. Sci. vol. 94 (1997) pp. 680–683.

Satoh et al. "Role of poly(ADP–ribose) formation in DNA repair" Nature vol. 356 (1992) p. 356.

Shaw "ADP–ribose in DNA Repair: A New Component of DNA Excision Repair" Advances in Radiation Biology (1984) pp. 1–69.

Ikai et al. "Localization of Poly(ADP–Ribose) Synythetase" J. Histochem. Cytochem vol. 31 (1983) pp. 1262–1264.

Denkewalter et al. Fortschritte der Arzneimittelforschung Progress in Drug Research Progrès des receherches pharmaceutiques vol. 10. (1996) pp. 224–285.

Pellicciari et al. "Homolytic Substitution and Carbenoidic Reactions in the Preparation of Benzimidazole Derivatives of Pharmaceutical Interest: Synthesis and Properties of (2–Cycloalkyl–1–benzimidazolyl)–N,N–diethylacetamides–" Arch. Pharm. vol. 318 (1985) pp. 393–399.

von der Saal et al. "Nonsteroidal Cardiotonics. 2. The Intropic Activity of Linear, Tricyclic 5–6–5 Fused Heterocycles" J. Med. Chem. (1989) pp. 1481–1491.

Forsberg et al. "Use Lantanide (III) Ions as Catalysts for the Reactions of Amines with Nitriles" J. Org. Chem. vol. 52 (1987) pp. 1017–1021.

Kawamitsu et al. "Monoclonal Antibodies to Poly(adenosine diphosphate ribose) Recognize Different Structures" Biochemistry vol. 23 (1984) pp. 3771–3777.

\* cited by examiner

CYCLO-ALKYL SUBSTITUTED BENZIMIDAZOLES AND THEIR USE AS PARP INHIBITORS

The present invention relates to novel benzimidazoles, their preparation and the use as inhibitors of the enzyme poly(ADP-ribose) polymerase or PARP (EC 2.4.2.30) for producing drugs.

Poly(ADP-ribose) polymerase (PARP) or, as it is also called, poly(ADP-ribose) synthase (PARS) is a regulatory enzyme found in cell nuclei (K. Ikai et al., *J. Histochem. Cytochem.* 1983, 31, 1261–1264). It is assumed that PARP is involved in the repair of DNA breaks (M. S. Satoh et al., *Nature* 1992, 356, 356–358). Damage or breaks in DNA strands activate the enzyme PARP which, when it is activated, catalyzes the transfer of ADP-ribose from NAD (S. Shaw, *Adv. Radiat. Biol.*, 1984, 11, 1–69). During this, nicotinamide is released from NAD. Nicotinamide is converted back into NAD by other enzymes with consumption of the energy carrier ATP. Overactivation of PARP would accordingly result in a non-physiologically large consumption of ATP, and this leads in the extreme case to cell damage and cell death.

It is known that free radicals such as superoxide anion, NO and hydrogen peroxide may lead to DNA damage in cells and thus activate PARP. The formation of large amounts of free radicals is observed in a number of pathophysiological states, and it is assumed that this accumulation of free radicals leads or contributes to the observed cell or organ damage. This includes, for example, ischemic states of organs as in stroke, myocardial infarct (C. Thiemermann et al., *Proc. Natl. Acad. Sci. USA*, 1997, 94, 679–683) or ischemia of the kidneys, but also reperfusion damage as occurs, for example, after lysis of myocardial infarct (see above: C. Thiemermann et al.). Inhibition of the enzyme PARP might accordingly be a means of at least partly preventing or modifying this damage. PARP inhibitors might thus represent a novel therapeutic principle for treating a number of diseases.

PARP influences the repair of DNA damage and thus might also play a part in the therapy of cancers, since a greater action potential on tumor tissues was observed (G. Chen et al. *Cancer Chemo. Pharmacol.* 1988, 22, 303) in combination with substances with cytostatic activity.

Non-limiting examples of tumors are leukemia, glioblastomas, lymphomas, melanomas, and carcinomas of the breast and cervix.

It has also been found that PARP inhibitors may show an immunosuppressant effect (D. Weltin et al. *Int. J. Immunopharmacol.* 1995, 17, 265–271).

It has likewise been discovered that PARP is involved in immunological disorders or diseases in which the immune system plays an important part, such as, for example, rheumatoid arthritis and septic shock, and that PARP inhibits may show a beneficial effect on the course of the disease (H. Kröger et al. *Inflammation* 1996, 20, 203–215; W. Ehrlich et al. *Rheumatol. Int.* 1995, 15, 171–172; C. Szabo et al., *Proc. Natl. Acad. Sci. USA* 1998, 95, 3867–3872; S. Cuzzocrea et al. *Eur. J. Pharmacol.* 1998, 342, 67–76).

PARP is understood to include for the purpose of this invention isoenzymes of the PARP enzyme described above.

PARP inhibitor 3-aminobenzamide showed protective effects in a model of circulatory failure (S. Cuzzocrea et al., *Br. J. Pharmacol.* 1997, 121, 1065–1074).

There is also experimental evidence that inhibitors of the enzyme PARP might be of benefit as agents for treating diabetes mellitus (V. Burkart et al. *Nature Med.* 1999, 5, 314–319).

Benzimidazoles have been described many times. Thus, DE 38 30 060 disclosed alkylated derivatives as inhibitors of erythrocyte aggregation. DE 35 22 230 mentions an ester derivative of 2-phenylbenzimidazole as inhibitor of platelet aggregation. Halogen-substituted 2-phenylbenzimidazoles having substituted amine residues on the phenyl ring have been described in WO 98/06703 as MCP-1 antagonists.

Also known are 2-phenylbenzimidazoles in which the benzimidazole group is substituted by an amide group. 5-Amido derivatives of 2-phenylbenzimidazole with alkoxy radicals on the phenyl ring have been described in WO 94/12461 as inhibitors of cAMP phosphodiesterase. It was found in DE 35 46 575 (e.g. Example 15) for analogous derivatives that these compounds induce positive inotropic effects. 4-Amido derivatives having a pyridyl radical in position 3 are likewise mentioned in WO 97/48697 as inhibitors for cAMP phosphodiesterase.

The synthesis of 2-phenylbenzimidazole-4-carboxamides has been described in J. Chem. Soc. Perkin Trans 1, 1979, 2303–2307. Analogous compounds which have a substituted alkyl chain on the amid residue and are said to have a cytotoxic effect are mentioned in J. Med. Chem. 1990, 33, 814–819. WO 97/04771 on the other hand mentions benzimidazole-4-carboxamides which inhibit PARS. In particular, derivatives described therein as active have a phenyl ring in position 2, and the phenyl ring may also be substituted by simple substituents such as nitro, methoxy and $CF_3$. Although some of these substances show good inhibition of the enzyme PARP, the derivatives described therein have the disadvantage that they show little or no solubility in aqueous solutions and thus cannot be administered as aqueous solution.

Benzimidazoles with cycloalkyl radicals in position 2 have likewise been described. Thus, 2-cyclohexyl derivatives which may also have alkylamides in position 1 are mentioned in F. Pellicciari et al., *Arch. Pharm.* 1985, 318, 393–399, or in *Ann.* 1952, 575, 162, which also described methyl derivatives in which the methyl group is located on the benzimidazole aromatic system. 2-Cycloalkylbenzimidazoles in which the aromatic ring is substituted by chlorine or nitro groups are described, for example, in DE 2649125, E. Seuer et al., *Farmaco* 1997, 52, 99 and M. Benchidmi et al., *Bull. Soc. Chim. Belg.* 1995, 104, 605–612. Derivatives of benzimidazole-5-carboxylic acid with cyclopentanedione residues in position 2 are mentioned in *Ann.*, 1893, 273, 320. Benzimidazoles with lactam rings fused to the aromatic ring have been described in DE 2732951 and in W. Saal et al., *J. Med. Chem.* 1989, 32, 1481–1491. However, benzimidazoles with carbocyclic rings in position 2 having an amide group on the benzimidazole ring or, in particular, position 4 on the benzimidazole ring have not yet been described.

In a number of therapies, such as strokes, the active substances are administered intravenously as infusion solution. For this purpose it is necessary to have available substances, in this case PARP inhibitors, which have adequate solubility in water at physiological pH values or close pH values (for example pH values of 5–8), so that an infusion solution can be prepared. Many of the PARP inhibitors described, especially the more effective PARP inhibitors, have the disadvantage, however, that they have only low or no solubility in water at these pH values and thus are unsuitable for intravenous administration. Active substances of this type can be administered only with excipients intended to promote solubility in water (cf. WO 97/04771). These excipients, for example polyethylene glycol and dimethyl sulfoxide, often cause side effects or are not tolerated.

Very effective PARP inhibitors with adequate solubility in water have not previously been described.

Surprisingly, it has been found that benzimidazoles having a saturated or monounsaturated carbocyclic system on the imidazole ring are very effective inhibitors but, owing to the further incorporation of aliphatic amine residues, they can form salts with acids and thus show distinctly improved solubility in water.

The present invention describes benzimidazole derivatives of th general formula I or II which are potent PARP inhibitors and also show adequate solubility in water to allow administration as infusion solution.

The present invention relates to substituted benzimidazoles of the general formula I and II:

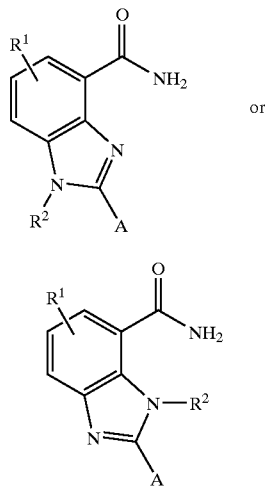

in which

A is a saturated or monounsaturated carbocyclic system which has 3 to 8 carbon atoms and may additionally have a fused-on benzene ring, it being possible for the rings also to be substituted by one or two different or identical radicals $R^3$ and also the radical $R^4$, and $R^1$ is hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$, O—$C_1$–$C_4$-alkyl where $R^{11}$ and $R^{12}$ are, independently of one another, hydrogen or $C_1$–$C_4$-alkyl, and $R^{13}$ is hydrogen, $C_1$–$C_4$-alkyl, $C_1$–$C_4$-alkyl-phenyl or phenyl, and $R^2$ is hydrogen, branched or unbranched $C_1$–$C_6$-alkyl, $C_1$–$C_4$-alkyl-phenyl and $R^3$ is $C_1$–$C_6$-alkyl, OH, O—$C_1$–$C_4$-alkyl, O—$C_1$–$C_4$-alkyl-phenyl, $NR^{11}R^{12}$, phenyl, $C_1$–$C_4$-alkyl-phenyl, $CF_3$, COOH, COO$C_1$–$C_4$-alkyl, CONH—$C_1$–$C_4$-alkyl, $CONH_2$, it being possible for the phenyl rings also to be substituted by a maximum of two identical or different radicals $R^{31}$, and $R^{31}$ is OH, $C_1$–$C_6$-alkyl, O—$C_1$–$C_4$-alkyl, chlorine, bromine, iodine, fluorine, $CF_3$, nitro, $NR^{11}R^{12}$, and $R^4$ is —$(O)_p$—$(CH_2)_q$—B, where B is $NR^{41}R^{42}$ and

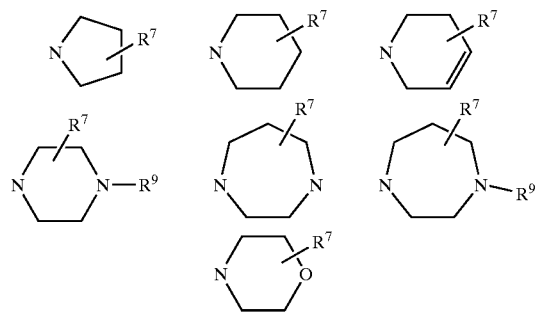

where p can be 0 and 1, and q can be 0, 1, 2 or 3, where if q is 0 p is also 0, and $R^{41}$ is hydrogen, $C_1$–$C_6$-alkyl, $(CH_2)_r$—E and $R^{42}$ is hydrogen, $C_1$–$C_6$-alkyl, —CO—$R^8$, $SO_2$—$R^8$, —(C=NH)—$R^8$ and —(C=NH)—$NHR^8$ and r is 0,1,2,3,4 and E is phenyl which may also carry a maximum of two radicals $R^{72}$, and, if r≠0,1, also $NR^{11}R^{12}$, NH—$C_1$–$C_4$-alkyl-phenyl, pyrrolidine, piperidine, dihydropiperidine, morpholine, homopiperidine, piperazine, which may also be substituted by $C_1$–$C_6$-alkyl and $C_1$–$C_4$-alkyl-phenyl, and homopiperazine, which may also be substituted by $C_1$–$C_6$-alkyl and $C_1$–$C_4$-alkyl-phenyl, and $R^7$ is hydrogen, $C_1$–$C_6$-alkyl, phenyl, it being possible for the ring also to be substituted by up to two identical or different radicals $R^{71}$, and $R^{71}$ is OH, $C_1$–$C_6$-alkyl, O—$C_1$–$C_4$-alkyl, chlorine, bromine, iodine, fluorine, $CF_3$, nitro, $NR^{11}R^{12}$, and $R^{72}$ is OH, $C_1$–$C_6$-alkyl, O—$C_1$–$C_4$-alkyl, chlorine, bromine, iodine, fluorine, $CF_3$, nitro, $NR^{11}R^{12}$, and $R^8$ is $C_1$–$C_6$-alkyl, phenyl, $C_1$–$C_4$-alkyl-phenyl, O—$C_1$–$C_4$-alkyl-phenyl, it being possible for the ring also to be substituted by up to two identical or different radicals $R^{81}$, and $R^{81}$ is OH, $C_1$–$C_6$-alkyl, O—$C_1$–$C_4$-alkyl, chlorine, bromine, iodine, fluorine, $CF_3$, nitro, $NR^{11}R^{12}$, and $R^9$ is hydrogen, $C_1$–$C_6$-alkyl, $C_1$–$C_4$-alkyl-phenyl, phenyl, it being possible for the rings also to be substituted by up to two radicals $R^{91}$, and $R^{91}$ can be OH, $C_1$–$C_6$-alkyl, O—$C_1$–$C_4$-alkyl, chlorine, bromine, iodine, fluorine, $CF_3$, nitro, $NR^{11}R^{12}$.

Carbocyclic systems which are at least monosubstituted are preferred for A. Preferred carbocyclic systems are: tetralin, indane, cycloheptane, cyclohexane, cyclopentane, cyclobutane and cyclopropane.

Preferred compounds of formulae I and II are those where A is a cyclohexane ring, $R^1$, $R^2$ and $R^3$ are hydrogen, and $R^4$ has the meaning as above, with p being 0 and 1 and q being 0, 1 and 2, $R^{41}$ and $R^{42}$ are, independently of one another, hydrogen and $C_1$–$C_4$-alkyl, $R^7$ is hydrogen, $C_1$–$C_4$-alkyl and phenyl, $R^9$ is hydrogen, $C_1$–$C_4$-alkyl and $C_1$–$C_2$-alkyl-phenyl, and $R^4$ can be in position 3 and 4 on the cyclohexane ring including both the cis and the trans forms or mixtures thereof.

Particularly preferred compounds of formulae I and II are those where A is a cyclohexane ring, and $R^1$, $R^2$ and $R^3$ are hydrogen, and $R^4$ has the meaning as above, with p being 0 and 1 and q being 0, 1 and 2, and $R^{41}$ and $R^{42}$ being, independently of one another, hydrogen and $C_1$–$C_4$-alkyl, $R^7$ is hydrogen, $R^9$ is hydrogen, $C_1$–$C_4$-alkyl and benzyl, and $R^4$ can be in position 4 on the cyclohexane ring, including both the cis and the trans forms and mixtures thereof.

The compounds of the formula I and II can be employed as racemates, as enantiomerically pure compounds or as diastereomers. Unless enantiomerically pure compounds are required, these can be obtained, for example, by carrying out a classical racemate resolution with a suitable optically active base or acid with the compounds of the formula I and II or their intermediates.

The invention also relates to compounds which are mesomers or tautomers of compounds of formula I.

The invention further relates to the physiologically tolerated salts of compounds I and II which can be obtained by reacting compounds I with a suitable acid or base. Suitable acids and bases are listed, for example, in Fortschritte der Arzneimittelforschung, 1966, Birkhäuser Verlag, Vol. 10, pp. 224–285. These include, for example, hydrochloric acid, citric acid, tartaric acid, lactic acid, phosphoric acid, methanesulfonic acid, formic acid, acetic acid, maleic acid, fumaric acid etc., and sodium hydroxide, lithium hydroxide, potassium hydroxide and tris.

Prodrugs mean compounds which are metabolized in vivo to compounds of the general formula I and II. Typical prodrugs are phosphates, carbamates of amino acids, esters and others.

The benzimidazoles I and II can be prepared in various ways, as outlined in synthesis schemes 1–3.

Synthesis scheme 1

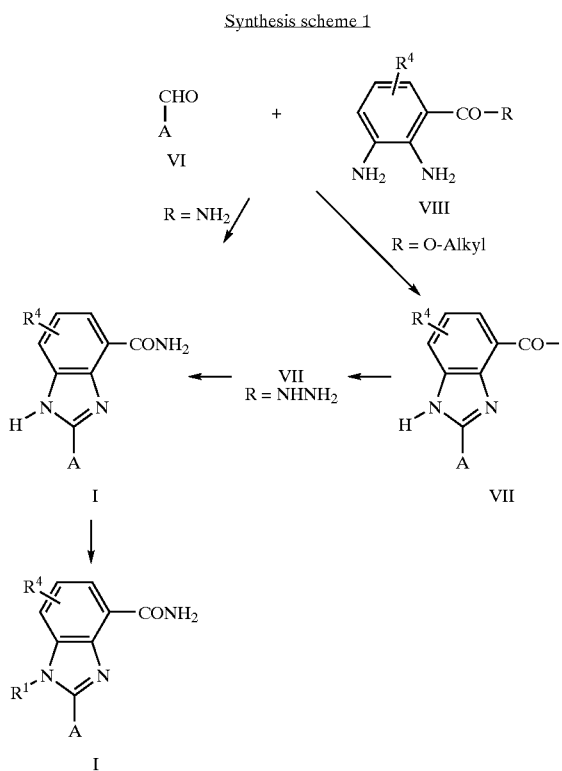

Condensation of the aldehyde with phenylenediamines results in the benzimidazole VII, this preferably being done in polar solvents such as ethanol or dimethylformamide with addition of acids such as acetic acid at elevated temperature, ordinarily 80–120° C. It is beneficial for the reaction to add weak oxidizing agents such as copper(II) salts, which are added as aqueous solution.

Synthesis scheme 2

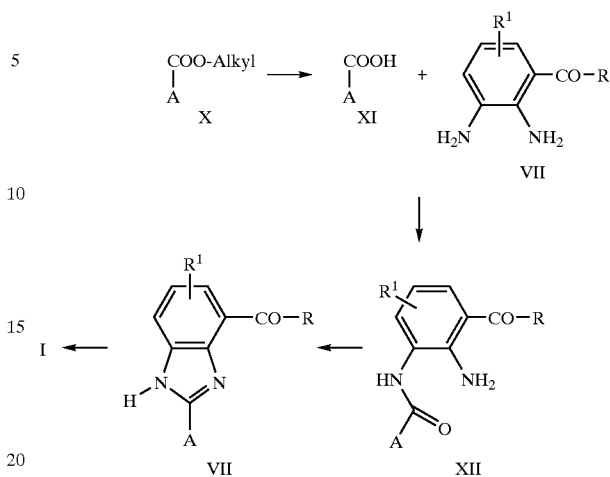

When R in the phenylenediamine VIII is $NH_2$, the condensation results directly in novel compounds I. Otherwise, if R is O-alkyl, this ester can be reacted with ammonia, where appropriate at elevated temperature and under elevated pressure, to give the amide I. Alternatively, the ester VIII can be reacted with hydrazine in polar solvents such as the alcohols butanol and ethanol or else dimethylformamide, at elevated temperatures, preferably 80–130° C., resulting in a hydrazide VIII ($R=NHNH_2$), which can then be reduced, such as with Raney nickel in alcohols under reflux, to the amide I.

$R^2$ is introduced into the benzimidazole residue in I ($R^2=H$) under alkylating conditions as above (see V–VI), although it is necessary to employ the reactant $R^2$—L (L=leaving group as above) (see Scheme 1).

Synthesis scheme 3

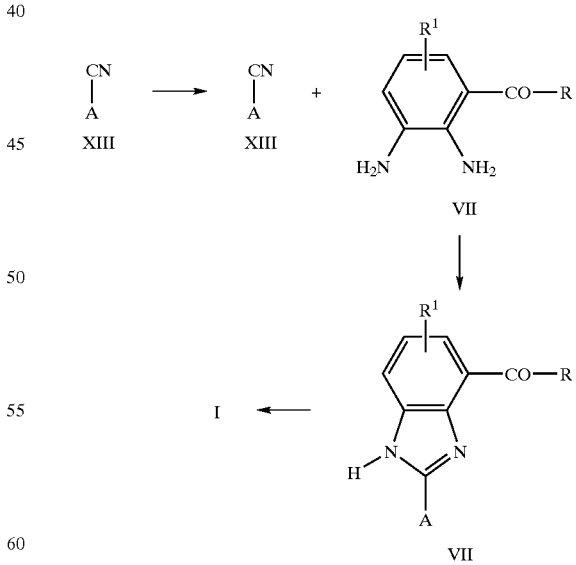

As an alternative to the aldehydes VI shown in scheme 1, it is also possible to employ acids such as XI (see Scheme 2) or nitriles such as XIV (see Scheme 3) in place of the aldehyde. These derivatives are prepared in analogy to the preparation of the substituted aldehydes VI. Starting from XI, the condensation to VII takes place in two stages. Firstly, the acid XI is reacted with the aniline VIII in a peptide-like coupling to give the amide XII. Conventional conditions are used for this, which are listed, for example, in Houben-Weyl, Methoden der organischen Chemie, 4$^{th}$ edition, E5, Chapter V or R. C. Larock, Comprehensive Organic Transformations, VCH Publisher, 1989, pages 972 et seq. The ring closure to the benzimidazole then takes place at elevated temperature, for example 60–180° C., with or without solvents such as dimethylformamide, and with the addition of acids such as acetic acid or directly in acetic acid itself.

Reaction of the phenylenediamine VIII with a nitrile XIV likewise takes place under conventional conditions. It is moreover possible to use solvents such as dimethylformamide with the addition of acids or else use polyphosphoric acid at elevated temperature, such as 60–200° C. However, it is also possible to use the conventional methods for preparing amidines from benzonitriles, as described in Houben-Weyl, Methoden der organischen Chemie, E5, pages 1304 et seq., J. Amer. Chem. Soc. 1957, 427 and J. Org. Chem. 1987, 1017.

The abovementioned substituted benzimidazoles I and II are inhibitors of the enzyme poly(ADP-ribose)polymerase or PARP (EC 2.4.2.30).

The inhibitory effect of the aforementioned substituted benzimidazoles I and II can be determined using an enzyme assay disclosed in the literature, with a $K_i$ being determined as gage of the effect. The benzimidazoles I and II were measured in this way for an inhibitory effect on the enzyme poly(ADP-ribose) polymerase or PARP (EC 2.4.2.30).

The substituted benzimidazoles of the general formulae I and II are inhibitors of poly(ADP-ribose) polymerase (PARP) or, as it also called, poly(ADP-ribose) synthase (PARS) and can thus be used for the treatment and prophylaxis of diseases associated with an elevated activity of these enzymes.

The compounds of the formulae I and II can be employed to produce drugs for treating damage following ischemias and for the prophylaxis of expected ischemias in various organs.

The present benzimidazoles of the general formulae I and II can accordingly be used for the treatment and prophylaxis of neurodegenerative diseases occurring after ischemia, trauma (craniocerebral trauma), massive bleeding, subarachnoid hemorrhages and stroke and of neurodegenerative diseases such as multi-infarct dementia, Alzheimer's disease, Huntington's disease and of epilepsies, in particular of generalized epileptic seizures, such as, for example, petit mal and tonoclonic seizures and partial epileptic seizures such as temporal lobe, and complex partial seizures, and further for the treatment and prophylaxis of damage to the heart after cardiac ischemia and damage to the kidneys after renal ischemia, for example of acute renal insufficiency, of acute kidney failure or of damage occurring during and after a kidney transplant. The compounds of the general formulae I and II can further be used to treat acute myocardial infarct and damage occurring during and after medical lysis thereof (for example with TPA, reteplase, streptokinase or mechanically with a laser or Rotablator) and of microinfarcts during and after heart valve replacement, aneurysm resections and heart transplants. It is likewise possible to use the present benzimidazoles I and II for treatment in cases of revascularization of critically narrowed coronary arteri s, for example in PTCA and bypass operations, and critically narrowed peripheral arteries, for example leg arteries. In addition, the benzimidazoles I and II can be beneficial in the chemotherapy of tumors and metastasis thereof and can be used to treat inflammations and rheumatic disorders such as, for example, rheumatoid arthritis.

The pharmaceutical preparations according to the invention comprise a therapeutically effective amount of the compounds I and II in addition to conventional pharmaceutical excipients.

For local external use, for example in dusting powders, ointments or sprays, the active ingredients can be present in the usual concentrations. The active substances are ordinarily present in an amount of from 0.001 to 1% by weight, preferably 0.001 to 0.1% by weight.

On internal use, the preparations are administered in single doses. From 0.1 to 100 mg are given per kg of body weight in a single dose. The preparation may be administered in one or more doses each day, depending on the nature and severity of the disorders.

Appropriate for the required mode of administration, the pharmaceutical preparations according to the invention comprise conventional carriers and diluents in addition to the active ingredient. For local external use it is possible to use pharmaceutical excipients such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is also possible for antioxidants such as tocopherol and butylated hydroxyanisole and butylated hydroxytoluene, flavor-improving additives, stabilizers, emulsifiers and lubricants to be present.

The substances present besides the active ingredient in the preparation, and the substances used during production of the pharmaceutical preparations, are toxicologically acceptable and compatible with the particular active ingredient. The pharmaceutical preparations are produced in a conventional way, for example by mixing the active ingredient with conventional excipients and diluents.

The pharmaceutical preparations can be administered in various ways, for example orally, parenterally such as intravenously by infusion, subcutaneously, intraperitoneally and topically. Thus, possible presentations are tablets, emulsions, infusion and injection solutions, pastes, ointments, gels, creams, lotions, dusting powders and sprays.

EXAMPLE A

Inhibition of the Enzyme Poly(ADP-ribose) Polymerase or PARP (EC 2.4.2.30)

A 96-well microtiter plate (Falcon) is coated with histones (type II-AS; SIGMA H7755). For this purpose, histones are dissolved in carbonate buffer (0.05 M $NaHCO_3$; pH 9.4) to a concentration of 50 µg/ml. The individual wells of the microtiter plate are each incubated with 100 µl of this histone solution overnight. The histone solution is then removed, and the individual wells are incubated with 200 µl of a 1% strength BSA (Bovine Serum Albumin) solution in carbonate buffer at room temperature for 2 hours. This is followed by three washes with washing buffer (0.05% Tween 10 in PBS). For the enzyme reaction, 50 µl of the enzyme reaction solution (5 µl of reaction buffer (1M Tris-HCl pH 8.0, 100 mM $MgCl_2$, 10 mM DTT), 0.5 µl of PARP (c=0.22 µg/µl), 4 µl of activated DNA (SIGMA D-4522, 1 mg/ml in water), 40.5 µl $H_2O$) are preincubated with 10 µl of an inhibitor solution in each well for 10 minutes. The enzyme reaction is started by adding 40 µl of a substrate solution (4 µl of reaction buffer (see above), 8 µl of NAD solution (100 µM in $H_2O$), 28 µl of $H_2O$). The reaction time is 20 minutes at room temperature. The reaction is stopped by washing three times with washing buffer (see above). This is followed by incubation with a specific anti-poly-ADP-ribose antibody at room temperature for one hour. The antibodies used were monoclonal anti-poly-(ADP-ribose) antibodies "10H" (Kawamaitsu H et al. (1984) Monoclonal antibodies to poly (adenosine diphosphate ribose) recognize different structures. Biochemistry 23, 3771–3777). It is likewise possible to use polyclonal antibodies.

The antibodies were used in a 1:5000 dilution in antibody buffer (1% BSA in PBS; 0.05% Tween20). Three washes with washing buffer were followed by incubation with the secondary antibody at room temperature for one hour. The monoclonal antibody used for this was an anti-mouse IgG coupled with peroxidase (Boehringer Mannheim) and the rabbit antibody was an anti-rabbit IgG coupled with peroxidase (SIGMA A-6154), each in a 1:10,000 dilution in antibody buffer. Three washes in washing buffer are followed by color reaction using 100 µl/well of color reagent (SIGMA, TMB mix, T8540) at room temperature for about 15 min. The color reaction is stopped by adding 100 µl of 2M $H_2SO_4$. Measurement takes place immediately thereafter (450 nm versus 620 nm; ELISA "Easy Reader" $EAR^{340}AT$ plate reader, SLT-Labinstruments, Austria). The $IC_{50}$ of an inhibitor to be measured is the inhibitor concentration at which a half-maximum change in color concentration occurs.

EXAMPLE B

Determination of the Solubility in Water

A compound to be measured is dissolved directly in a fixed volume of water, and the resulting solution is adjusted to pH 5–6 with a sodium acetate solution, so that the active ingredient concentration to be tested is reached. If the measured substance is not in the form of a water-soluble salt, it was dissolved in the minimum amount of dimethyl sulfoxide and then diluted with water (final dimethyl sulfoxide concentration $\leq 1\%$), after which the pH was again adjusted. The potent PARP inhibitor NU 1076 (WO 97/04771) showed a solubility <0.01% in this test, whereas Example 1 according to the invention has a solubility >0.5%.

EXAMPLES

Example 1

2-(cis-4-Amino-1-cyclohexyl)benzimidazole-4-carboxamide×2 HCl a) Methyl 2-amino-3-(cis-4-amino-1-cyclohexylamino) benzoate 2.4 g (9.9 mmol) of cis-4-(tert-butoxycarbonylamino)-cyclohexanecarboxylic acid and 2.7 ml (19.7 mmol) of triethylamine were dissolved in 70 ml of anhydrous tetrahydrofuran and, at −10° C., a solution of 0.94 ml (9.9 mmol) of ethyl chloroformate in 25 ml of anhydrous tetrahydrofuran was added dropwise. The mixture was then stirred at 0° C. for 1 hour. After this, 1.6 g (9.9 mmol) of methyl 2,3-diaminobenzoate were added, and the mixture was stirred at room temperature for 16 hours. The reaction mixture was poured into ice-water and made alkaline with aqueous sodium bicarbonate solution. This aqueous phase was extracted with ethyl acetate. The organic phase was then washed with aqueous sodium bicarbonate solution and water, dried and concentrated in vacuo. 2.7 g of the product were obtained.

b) Methyl 2-(cis-4-amino-1-cyclohexyl)benzimidazole-4-carboxylate 2.6 g of the product 1a were refluxed in 80 ml of acetic acid for 1 hour. The reaction mixture was concentrated in vacuo, and the resulting precipitate was partitioned between ethyl acetate and aqueous sodium carbonate solution. The organic phase was washed with water, dried and concentrated in vacuo. The resulting residue was purified by chromatography (eluent: ethyl acetate/methanol=3/1), resulting in 0.7 g of the product.

c) 2-(cis-4-Amino-1-cyclohexyl)benzimidazole-4-carbohydrazide 0.65 g of the product from procedure 1b were refluxed with 0.6 g (11.9 mmol) of hydrazine hydrate in 5 ml of ethanol for 90 minutes. The mixture was then concentrated in vacuo, resulting in a crude product which was reacted without further purification.

d) 2-(cis-4-Amino-1-cyclohexyl)benzimidazole-4-carboxamide×2 HCl

The product from 1c was added dropwise to a dispersion of 2 g of Raney nickel/water and 20 ml of dimethylformamide. The mixture was refluxed for 1 hour. After cooling, the Raney nickel was filtered off and the filtrate was concentrated in vacuo. The residue was treated with water, and the resulting precipitate was filtered off with suction. The precipitate was dissolved in isopropanol, and ethereal hydrochloric acid was added. The resulting precipitate was filtered off with suction. 0.19 g of the product was obtained.

$^1$H-NMR ($D_6$-DMSO). δ =1.7 (2H), 1.9 (4H), 2.2–2.4 (4H), 3.4 (2H), 7.6 (1H) and 7.9 (1H) ppm.

Example 2

2-(3-Methoxycyclohexyl)benzimidazole-4-carboxamide a) 6-Nitro-2-carboxybenzamide 52.5 g (0.27 mol) of 3-nitrophthalic anhydride were stirred in portions over the course of 30 minutes into 75 ml of concentrated aqueous ammonia at room temperature. The mixture was then cooled to 0° C., after which a precipitate crystallized out and was filtered off with suction. This precipitate was dissolved in 125 ml of water by gently heating, and 25.6 ml of 32% strength hydrochloric acid were rapidly added. The mixture was cooled to 0° C., and the crystals which separated out were filtered off with suction. 45 g of the product were obtained.

b) 2-Amino-3-nitrobenzoic Acid 109 g (1.9 mol) of potassium hydroxide were dissolved in 400 ml of water and, at 0° C., 11 ml (0.22 mol) of bromine were added dropwise. Then 45 g (0.21 mol) of the intermediate 2a were added over the course of 1 hour. The reaction solution was then stirred at 60° C. for 1 hour and subsequently at room temperature for 16 hours. The pH of the solution was adjusted to 5–6 by adding hydrochloric acid, after which the product precipitates. 30.8 g of the product were obtained.

c) Ethyl 2-amino-3-nitro-benzoate 30.8 g (0.17 mol) of the intermediate 2b were added to 170 ml of ethanol and, after cautious addition of 20 ml of concentrated sulfuric acid, refluxed for 24 hours. The mixture was then cautiously added to an ice/aqueous ammonia mixture, whereupon the product precipitates. 28.8 g of the product were obtained.

d) Ethyl 2,3-diaminobenzoate 28.8 g (0.14 mol) of the intermediate 2c were hydrogenated in 200 ml of ethanol after addition of 1 g of palladium/carbon (10%). The mixture was filtered, and the filtrate was concentrated in vacuo. 23.5 g of the product were obtained.

e) 2,3-Diaminobenzamide×2 HCl 23.5 g (0.13 mol) of the intermediate 2d were heated in 260 ml of n-butanol after addition of 50 ml of hydrazine hydrate at 100° C. for 16 hours. The mixture was then concentrated in vacuo.

50 g of Raney nickel were suspended in 200 ml of dimethylformamide/water (1/1). The above vacuum residue was cautiously (evolution of gas) added to the suspension, and the mixture was heated at 100° C. for 8 hours. It was then filtered, and the filtrate was concentrated in vacuo. The residue was dissolved in a little methanol, and ether was added to incipient turbidity. A precipitate separates out and was filtered off. The filtrate was concentrated in vacuo. This residue was redissolved in methanol, and isopropanolic hydrogen chloride solution was cautiously added. The precipitated product was filtered off with suction. 31 g of the product were obtained.

f) 2-(3-Methoxycyclohexyl)benzimidazole-4-carboxamide 1.4 g (8.9 mmol) of 3-methoxycyclohexanecarboxylic acid were reacted in analogy to method 3a with the intermediate 2e, and the material obtained in this way was cyclized in analogy to method 3b. 0.2 g of the product was obtained.

$^1$H-NMR (D$_6$-DMSO): δ=1.1–2.3 (8H), 3.2 (1H), 3.3 (3H), 3.6 (1H), 7.2 (1H), 7.6 (1H), 7.65 (1H), 7.7 (1H) and 9.2 (1H) ppm Example 3

2(4-Methoxycyclohexyl)benzimidazole-4-carboxamide a) 2-Amino-3-(4-methoxycyclohexylamino)benzamide 1.4 g (8.9 mmol) of 4-methoxycyclohexanecarboxylic acid were dissolved in 30 ml of tetrahydrofuran and, at 0° C., successively 1.9 g (1.8 mmol) of N'-(3-dimethylaminopropyl)-N-ethylcarbodiimide× hydrochloride, 1.8 g (11.6 mmol) of N-hydroxybenzotriazole and 1.95 g (19.2 mmol) of triethylamine were added. The mixture was stirred for 1 hour. Then 2.0 g (8.9 mmol) of 2,3-diaminobenzamide×2 hydrochloride and 1.95 g (19.2 mmol) of triethylamine were added. The mixture was then stirred at 0° C. for 1 hour and at room temperature for 16 hours. The mixture was diluted with a large amount of water and extracted several times with ethyl acetate. The organic phases were combined, dried and concentrated in vacuo. 1.5 g of the product were obtained.

b) 2-(4-Methoxycyclohexyl)benzimidazole-4-carboxamide 1.3 g of the intermediate 3a were refluxed in 60 ml of concentrated acetic acid for 3 hours. The mixture was then concentrated in vacuo, and the residue was purified by chromatography (eluent: methanol/methylene chloride=1/20). 0.8 g of the product was obtained.

$^1$H-NMR (D$_6$-DMSO): δ=1.1–2.3 (8H), 2.9 (1H), 3.0 (1H), 3.25 (3H), 7.1 (1H), 7.5 (1H), 7.6 (1H), 7.75 (1H) and 9.2 (1H) ppm.

Example 4

2-(4-(2-(N,N-Diethylamino)ethoxy)cyclohexyl)benzimidazole-4-carboxamide×2 HCl a) Ethyl 4-(2-N,N-diethylamino)ethoxy)cyclohexanecarboxylate A solution of 1 g (58 mmol) of ethyl 3-hydroxycyclohexane-carboxylate in dimethylformamide was added dropwise to 2.7 g (64 mmol) of sodium hydride in dimethylformamide at room temperature. The mixture was stirred for 30 minutes. Then 7.8 g (58 mmol) of N-(2-chloroethyl)-N,N-diethylamine dissolved in dimethylformamide were added dropwise, and the mixture was stirred at room temperature for 16 hours. A little water was then cautiously added, and the mixture was subsequently concentrated in vacuo. The residue was partitioned between diethyl ether and water, and the organic solution was dried and concentrated in vacuo. The crude product obtained in this way was then purified by chromatography (eluent: methanol).

b) 4-(2-(N,N-Diethylamino)ethoxy)cyclohexanecarboxylic Acid 1.4 g (5.2 mmol) of the intermediate 4a were added to 15 ml of water/ethanol (2:1), and 0.4 g (10.3 mmol) of sodium hydroxide was added. The mixture was stirred at room temperature for 2 hours and then concentrated in vacuo. The resulting crude product was immediately reacted further.

c) 2-Amino-3-(4-(2-(N,N-diethylamino)ethoxy)cyclohexylamino)-benzamide 1.2 g (4.9 mmol) of the intermediate 4b were reacted in analogy to method 3a with 2,3-diaminobenzamide×2 HCl. The crude product was immediately reacted further.

d) 2-(4-(2-(N,N-Diethylamino)ethoxy)cyclohexyl)benzimidazole-4-carboxamide×2 HCl The crude product from 4c was reacted in analogy to method 3b. The product was purified by chromatography (eluent: methanol/methylene chloride=1/20+0.1% NH$_4$OH). The product was then converted into the hydrochloride.

$^1$H-NMR (D$_6$-DMSO): δ=1.2 (6H), 1.3–2.3 (8H), 2.9–3.5 (9H), 3.7 (1H), 3.8 (2H), 7.5 (1H), 7.8 (1H), 7.9 (1H), 8.0 (1H), 8.5 (1H) and 10.2 (broad) ppm The following were prepared in analogy to the methods of Examples 1 to 4:

Example 5 trans-2-(4-aminocyclohexyl)benzimidazole-4-carboxamide MS: m/e=256 (M$^+$)

Example 6 trans-2-(4-(aminomethyl)cyclohexyl)benzimidazole-4-carboxamide MS: m/e=270 (M$^+$)

Example 7

2-(4-methylcyclohexyl)benzimidazole-4-carboxamide MS: m/e=257 (M$^+$)

Example 8

2-(3-methylcyclohexyl)benzimidazole-4-carboxamide MS: m/e=257 (M$^+$)

Example 9

2-(2-methylcyclohexyl)benzimidazole-4-carboxamide MS: m/e=257 (M$^+$)

Example 10

2-(3-benzyloxyaminocyclohexyl)benzimidazole-4-carboxamide $^1$H-NMR (D$_6$-DMSO): δ=1.2–2.3 (8H), 3.1 (1H), 3.5 (1H), 5.0 (2H), 7.2–7.5 (6H), 7.7–7.9 (3H) and 9.4 (1H) ppm Example 11

2-(3-aminocyclohexyl)benzimidazole-4-carboxamide× HCl

¹H-NMR (D₆-DMSO): δ=1.3–2.3 (8H), 3.5 (1H), 3.7 (1H), 7.7 (1H) and 7.9 (2H) ppm

The following compounds can be prepared by the methods described above:

1. 2-(cis-4-carboxy-1-cyclohexyl)benzimidazole-4-carboxamide
2. 2-(trans-4-carboxy-1-cyclohexyl)benzimidazole-4-carboxamide
3. 2-(4-tert-butyl-1-cyclohexyl)benzimidazole-4-carboxamide
4. 2-(2,4,6-trimethyl-1-cyclohexyl)benzimidazole-4-carboxamide
5. 2-(3-amino-2-methyl-1-cyclohexyl)benzimidazole-4-carboxamide
6. 2-(2-hydroxy-1-cyclohexyl)benzimidazole-4-carboxamide
7. 2-(trans-4-(1-pentyl)-1-cyclohexyl)benzimidazole-4-carboxamide
8. 2-(4-hydroxy-1-cyclohexyl)benzimidazole-4-carboxamide
9. 2-(cis-3-amino-1-cyclohexyl)benzimidazole-4-carboxamide
10. 2-(trans-3-amino-1-cyclohexyl)benzimidazole-4-carboxamide
11. 2-(4-(1-propyl)-1-cyclohexyl)benzimidazole-4-carboxamide
12. 2-(4-(1-butyl)-1-cyclohexyl)benzimidazole-4-carboxamide
13. 2-(4-tert-butyl-2-methyl-1-cyclohexyl)benzimidazole-4-carboxamide
14. 2-(3-carboxy-1-cyclohexyl)benzimidazole-4-carboxamide
15. 2-(cis-2-amino-1-cyclohexyl)benzimidazole-4-carboxamide
16. 2-(3-hydroxy-1-cyclohexyl)benzimidazole-4-carboxamide
17. 2-(4-trifluoromethyl-1-cyclohexyl)benzimidazole-4-carboxamide
18. 2-(2.6-dimethyl-4-hydroxy-1-cyclohexyl)benzimidazole-4-carboxamide
19. 2-(4-amino-2.6-dimethyl-1-cyclohexyl)benzimidazole-4-carboxamide
20. 2-(4-phenyl-1-cyclohexyl)benzimidazole-4-carboxamide
21. 2-(4-(4-chlorophenyl)-1-cyclohexyl)benzimidazole-4-carboxamide
22. 2-(trans-4-(tert-butoxycarbonylaminomethyl)-1-cyclohexyl)benzimidazole-4-carboxamide
23. 2-(4-amidinomethyl-1-cyclohexyl)benzimidazole-4-carboxamide
24. 2-(cis-4-carboxy-1-cyclohexyl)benzimidazole-4-carboxamide
25. 2-(4-(diethylamino)-1-cyclohexyl)benzimidazole-4-carboxamide
26. 2-(4-(dimethylamino)-1-cyclohexyl)benzimidazole-4-carboxamide
27. 2-(3-(diethylamino)-1-cyclohexyl)benzimidazole-4-carboxamide
28. 2-(3-(dimethylamino)-1-cyclohexyl)benzimidazole-4-carboxamide
29. 2-(4-(dimethylamino)-1-cyclohexyl)benzimidazole-4-carboxamide
30. 2-(cis-4-(diethylamino)-1-cyclohexyl)benzimidazole-4-carboxamide
31. 2-(trans-4-(diethylamino)-1-cyclohexyl)benzimidazole-4-carboxamide
32. 2-(cis-4-(dimethylamino)-1-cyclohexyl)benzimidazole-4-carboxamide
33. 2-(trans-4-(dimethylamino)-1-cyclohexyl)benzimidazole-4-carboxamide
34. 2-(4-(ethylamino)-1-cyclohexyl)benzimidazole-4-carboxamide
35. 2-(cis-4-(ethylamino)-1-cyclohexyl)benzimidazole-4-carboxamide
36. 2-(trans-4-(ethylamino)-1-cyclohexyl)benzimidazole-4-carboxamide
37. 2-(4-(methylamino)-1-cyclohexyl)benzimidazole-4-carboxamide
38. 2-(cis-4-(methylamino)-1-cyclohexyl)benzimidazole-4-carboxamide
39. 2-(trans-4-(methylamino)-1-cyclohexyl)benzimidazole-4-carboxamide
40. 2-(4-(propylamino)-1-cyclohexyl)benzimidazole-4-carboxamide
41. 2-(cis-4-(propylamino)-1-cyclohexyl)benzimidazole-4-carboxamide
42. 2-(trans-4-(propylamino)-1-cyclohexyl)benzimidazole-4-carboxamide
43. 2-(3-(ethylamino)-1-cyclohexyl)benzimidazole-4-carboxamide
44. 2-(3-methylamino)-1-cyclohexyl)benzimidazole-4-carboxamide
45. 2-(3-(propylamino)-1-cyclohexyl)benzimidazole-4-carboxamide
46. 2-(4-(N-ethyl-N-methylamino)-1-cyclohexyl)benzimidazole-4-carboxamide
47. 2-(3-(N-ethyl-N-methylamino)-1-cyclohexyl)benzimidazole-4-carboxamide
48. 2-(4-(N-ethyl-N-propylamino)-1-cyclohexyl)benzimidazole-4-carboxamide
49. 2-(3-(N-ethyl-N-propylamino)-1-cyclohexyl)benzimidazole-4-carboxamide
50. 2-(4-piperidin-1-yl-1-cyclohexyl)benzimidazole-4-carboxamide
51. 2-(3-piperidin-1-yl-1-cyclohexyl)benzimidazole-4-carboxamide
52. 2-(cis-4-piperidin-1-yl-1-cyclohexyl)benzimidazole-4-carboxamide
53. 2-(trans-4-piperidin-1-yl-1-cyclohexyl)benzimidazole-4-carboxamide
54. 2-(4-pyrrolidin-1-yl-1-cyclohexyl)benzimidazole-4-carboxamide
55. 2-(3-pyrrolidin-1-yl-1-cyclohexyl)benzimidazole-4-carboxamide
56. 2-(cis-4-pyrrolidin-1-yl-1-cyclohexyl)benzimidazole-4-carboxamide
57. 2-(trans-4-pyrrolidin-1-yl-1-cyclohexyl)benzimidazole-4-carboxamide
58. 2-(4-(4-methylpiperazin-1-yl-1-cyclohexyl)benzimidazole-4-carboxamide
59. 2-(3-(4-methylpiperazin-1-yl-1-cyclohexyl)benzimidazole-4-carboxamide
60. 2-(cis-4-(4-methylpiperazin-1-yl-1-cyclohexyl)benzimidazole-4-carboxamide 61. 2-(trans-4-(4-methylpiperazin-1-yl-1-cyclohexyl)benzimidazole-4-carboxamide
62. 2-(4-(piperazin-1-yl-1-cyclohexyl)benzimidazole-4-carboxamide
63. 2-(3-(piperazin-1-yl-1-cyclohexyl)benzimidazole-4-carboxamide
64. 2-(cis-4-(piperazin-1-yl-1-cyclohexyl)benzimidazole-4-carboxamide
65. 2-(trans-4-(piperazin-1-yl-1-cylcyclohexyl)benzimidazole-4-carboxamide
66. 2-(4-(4-benzylpiperazin-1-yl-1-cyclohexyl)benzimidazole-4-carboxamide
67. 2-(3-(4-benzylpiperazin-1-yl-1-cyclohexyl)benzimidazole-4-carboxamide
68. 2-(4-(4-phenylpiperazin-1-yl-1-cyclohexyl)benzimidazole-4-carboxamide
69. 2-(3-(4-phenylpiperazin-1-yl-1-cyclohexyl)benzimidazole-4-carboxamide
70. 2-(4-(4-propylpiperazin-1-yl-1-cyclohexyl)benzimidazole-4-carboxamide
71. 2-(3-(4-propylpiperazin-1-yl-1-cyclohexyl)benzimidazole-4-carboxamide
72. 2-(4-(4-butylpiperazin-1-yl-1-cyclohexyl)benzimidazole-4-carboxamide
73. 2-(3-(4-butylpiperazin-1-yl-1-cyclohexyl)benzimidazole-4-carboxamide
74. 2-(4-(4-homopiperazin-1-yl-1-cyclohexyl)benzimidazole-4-carboxamide
75. 2-(3-(4-homopiperazin-1-yl-1-cyclohexyl)benzimidazole-4-carboxamide
76. 2-(4-(4-(N-methylhomopiperazin-1-yl)-1-cyclohexyl)benzimidazole-4-carboxamide
77. 2-(3-(4-(N-methylhomopiperazin-1-yl)-1-cyclohexyl)benzimidazole-4-carboxamide
78. 2-(4-(4-(4-phenyl-1,2,5,6-tetrahydropyridin-1-yl-1-cyclohexyl)benzimidazole-4-carboxamide
79. 2-(3-(4-(4-phenyl-1,2,5,6-tetrahydropyridin-1-yl-1-cyclohexyl)benzimidazole-4-carboxamide

We claim:
1. A compound of the formula I or II

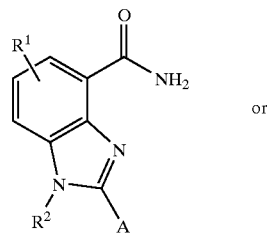

or

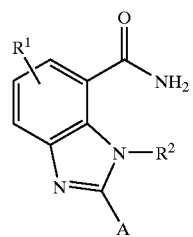

in which
A is a saturated or monounsaturated carbocyclic system which has 3 to 8 carbon atoms and may additionally have a fused-on benzene ring, it being possible for the rings also to be substituted by one or two different or identical radical $R^3$ and also the radical $R^4$, and $R^1$ is hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$ or O—$C_1$–$C_4$-alkyl where $R^{11}$ and $R^{12}$ are, independently of one another, hydrogen or $C_1$–$C_4$-alkyl, and $R^{13}$ is hydrogen, $C_1$–$C_4$-alkyl-phenyl or phenyl, and $R_2$ is hydrogen or branched and unbranched $C_1$–$C_6$-alkyl, and R3 is $C_1$–$C_6$-alkyl, OH, O—$C_1$–$C_4$-alkyl, O—$C_1$–$C_4$-alkyl-phenyl, $NR^{11}R^{12}$, phenyl, $C_1$–$C_4$-alkyl-phenyl, $CF_3$, COOH, COO$C_1$–$C_4$-alkyl, CONH—$C_1$–$C_4$-alkyl or $CONH_2$, it being possible for the phenyl rings also to be substituted by a maximum of two identical or different radicals $R^{31}$, and $R^{31}$ is OH, $C_1$–$C_6$-alkyl, O—$C_1$–$C_4$-alkyl, chlorine, bromine, iodine, fluorine, $CF_3$, nitro or $NR^{11}R^{12}$, and $R^4$ is —$(O)_p$—$(CH_2)_q$—B, where
B is $NR^{41}R^{42}$,

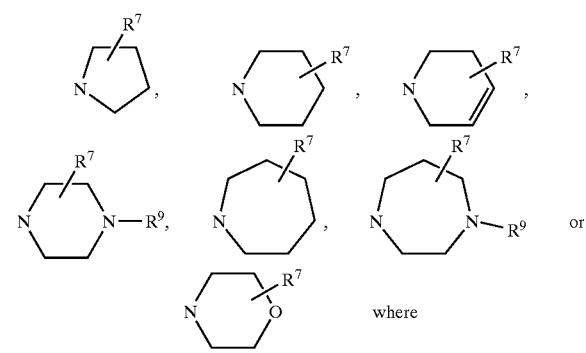

where p can be 0 or 1, and
q can be 0, 1, 2 or 3, where if q is 0 p is also 0, and
$R^{41}$ is hydrogen, $C_1$–$C_6$-alkyl or $(CH_2)_r$—E and
$R^{42}$ is hydrogen, $C_1$–$C_6$-alkyl, —CO—$R^8$, $SO_2$—$R^8$, —(C=NH)—$R^8$ or —(C=CH)—$NHR^8$ and
r is 0,1,2,3 or 4 and
E is phenyl which may also carry a maximum of two radicals $R^{72}$, and, if r?0 or 1, E is $NR^{11}R^{12}$, NH—$C_1$–$C_4$-alkyl-phenyl, pyrrolidine, piperidine, dihydropiperidine, morpholine, homopiperidine or piperazine, which may also be substituted by $C_1$–$C_6$-alkyl or
$C_1$–$C_4$-alkyl-phenyl, and homopiperazine, which may also be substituted by $C_1$–$C_6$-alkyl and $C_1$–$C_4$-alkyl-phenyl, and homopiperazine, which may also be substituted by C-$_1$–$C_6$-alkyl or $C_1$–$C_4$-alkyl-phenyl and $R^7$ is hydrogen, $C_1$–$C_6$-alkyl or phenyl, it being possible for the ring also to be substituted by up to two identical or different radicals $R^{71}$, and $R^{71}$ is OH, $C_1$–$C_6$-alkyl, O—$C_1$–$C_4$-alkyl, chlorine, bromine, iodine, fluorine, $CF_3$, nitro $NR^{11}R^{12}$ or $NHOC_1$–$C_4$-alkyl and $R^{72}$ is OH, $C_1$–$C_6$-alkyl, O—$C_1$–$C_4$-alkyl, chlorine, bromine, iodine, fluorine, $CF_3$, nitro, $NR^{11}R^{12}$ or $NHOC_1$–$C_4$-alkyl and $R^8$ is $C_1$–$C_6$-alkyl, phenyl, $C_1$–$C_4$-alkyl-phenyl or O—$C_1$–$C_4$-alkyl-phenyl, it being possible for the rings also to be substituted by up to two identical or different radicals, and $R^{81}$ is OH, $C_1$–$C_6$-alkyl, O—$C_1$–$C_4$-alkyl, chlorine, bromine, iodine, fluorine, $CF_3$ nitro r $NR^{11}R^{12}$, and $R^9$ is hydrogen, $C_1$–$C_6$-alkyl, $C_1$–$C_4$-alkyl-phenyl or phenyl, it being possible for the rings also to be substituted by up to two radicals $R^{91}$, and $R^{91}$ is OH, $C_1$–$C_6$-alkyl, O—$C_1$–$C_4$-alkyl, chlorine, bromine, iodine, fluorine, $CF_3$, nitro or $NR^{11}R^{12}$, or their tautomeric forms, possible enantiomeric or diastereomeric forms, and possible cistrans isomers on the rings in A.

2. A compound as claimed in claim 1, where A is substituted by at least one substituent $R^3$ or $R^4$.

3. A compound of the formula I or II as claimed in claim 1

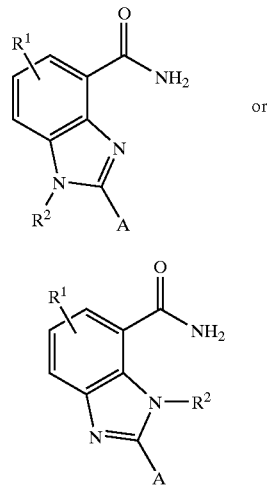

in which

A is tetralin, indane, cycloheptane, cyclopentane, cyclobutane and cyclopropane.

4. A compound as claimed in claim 1, where

A is cyclohexane and $R^1$, $R^2$ and $R^3$ are hydrogen and $R^4$ has the meaning as in claim 1, where p is 0 or 1 and q is 0, 1 or 2, $R^{41}$ and $R^{42}$ are, independently of one another, hydrogen or $C_1$–$C_4$-alkyl, $R^7$ is hydrogen, $C_1$–$C_4$-alkyl or phenyl, $R^9$ is hydrogen, $C_1$–$C_4$-alkyl or $C_1$–$C_2$-alkyl-phenyl, and $R^4$ can be in position 3 and 4 on the cyclohexane ring.

5. A pharmaceutical preparation comprising compounds of the formula I or II as claimed in claim 1, in addition to conventional carriers and excipients.

6. A method of treating a patient having a neuorodegenerative disease or neuronal damage comprising administering to said patient an effective amount of a compound of claim 1.

7. The method of claim 6 wherein the neurodegenerative diseases or neuronal damage are induced by ischemia, trauma or massive bleeding.

8. The method of claim 6 wherein the neurodegenerative disease or neuronal damage is stroke or craniocerebral trauma.

9. The method of claim 6 wherein the neurodegenerative disease or neuronal damage is Alzheimer's disease, Parkinson's disease or Huntington's disease.

10. A method of treating damage due to ischemia in a patient in need of such treatment comprising administering to said patient an effective amount of a compound of claim 1.

11. A method for treating a patient having epilepsy comprising administering to said patient an effective amount of a compound of claim 1.

12. A method for treating a patient having damage to the kidneys after renal ischemia or during and after kidney transplants comprising administering to said patient an effective amount of a compound of claim 1.

13. A method for treating a patient having damage to the heart after cardiac ischemia comprising administering to said patient an effective amount of a compound of claim 1.

14. A method for treating a patient having microinfarcts comprising administering to said patient an effective amount of a compound of claim 1.

15. A method of treatment in cases of a patient having revascularization of critically narrowed coronary arteries comprising administering to said patient an effective amount of a compound of claim 1.

16. A method for treating a patient having acute myocardial infarct or damage during and after medical or mechanical lysis thereof comprising administering to said patient an effective amount of a compound of claim 1.

17. A method for treating a patient having tumors or metastasis thereof comprising administering to said patient an effective amount of a compound of claim 1.

18. A method for treating a patient having sepsis or septic shock comprising administering to said patient an effective amount of a compound of claim 1.

19. A method for treating a patient having immunological diseases comprising administering to said patient an effective amount of a compound of claim 1.

20. A method for treating a patient having diabetes mellitus comprising administering to said patient an effective amount of a compound of claim 1.

21. The method of claim 11 wherein the epilepsy is a petit mal, tonoclonic valve replacement, aneurysm resection or heart transplant.

22. The method of claim 14 wherein the microinfarct is caused by heart valve replacement, aneurysm resection or heart transplant.

23. The method of claim 19 wherein the immunological disease is inflammation or rheumatoid arthritis.

* * * * *